United States Patent
Canós et al.

(10) Patent No.: US 7,419,830 B2
(45) Date of Patent: Sep. 2, 2008

(54) PLURAL REACTION CHAMBER CATALYTIC TESTING DEVICE AND METHOD FOR ITS USE IN CATALYST TESTING

(75) Inventors: Avelino Corma Canós, Valencia (ES); Jose Manuel Serra Alfaro, Valencia (ES); Juan Hernández Fenollosa, Valencia (ES)

(73) Assignee: Universidad Politecnia De Valencia, Madrid (ES)

( * ) Notice: Subject to any disclaimer, the term of this patent is extended or adjusted under 35 U.S.C. 154(b) by 831 days.

(21) Appl. No.: 10/212,669

(22) Filed: Aug. 5, 2002

(65) Prior Publication Data
US 2003/0040116 A1    Feb. 27, 2003

Related U.S. Application Data

(63) Continuation of application No. PCT/ES01/00038, filed on Feb. 8, 2001.

(30) Foreign Application Priority Data
Feb. 8, 2000    (ES)    ................... 200000352

(51) Int. Cl.
*G01N 31/10*    (2006.01)
*B01J 8/06*    (2006.01)
*B01J 8/18*    (2006.01)

(52) U.S. Cl. .............. 436/37; 422/62; 422/78; 422/83; 422/88; 422/108; 422/109; 422/110; 422/111; 422/129; 422/130; 422/131; 436/52; 436/85; 436/139; 436/141; 436/142; 436/161; 436/171; 436/172; 436/173

(58) Field of Classification Search ............ 436/37, 436/52, 127–131, 139–142, 149–152, 155, 436/159, 161, 171–173, 85; 422/62, 78, 422/81, 83, 88–92, 103, 129, 108–111, 130–131
See application file for complete search history.

(56) References Cited

U.S. PATENT DOCUMENTS 2,983,774 A  *  5/1961  Thompson .................. 585/372

(Continued)

FOREIGN PATENT DOCUMENTS

DE    2425227    *    3/1975

(Continued)

OTHER PUBLICATIONS

Creer, J. G. et al, Applied Catalysis 1986, 22, 85-95.*

(Continued)

*Primary Examiner*—Arlen Soderquist
(74) *Attorney, Agent, or Firm*—Klauber & Jackson

(57) ABSTRACT

A catalytic testing device comprising
 a reaction block comprising a set of reaction chambers, each chamber comprising a fluid inlet and outlet connected to an outgoing fluid duct connected to analysis means,
 fluid feed means capable of performing regulated dosing of flows of the fluid at the required pressure independently in each of the reaction chambers,
 automatic and dynamic pressure control means, capable of performing pressure regulation in each reaction chamber, which comprise
 a non-return valve in the outgoing fluid duct between the outlets of the reaction chambers and a common regulating tank that receives the outgoing fluid from the chambers,
 a pressure sensor provided in a first outlet duct and an automatic needle valve provided in a second outlet duct from the tank.

33 Claims, 2 Drawing Sheets

U.S. PATENT DOCUMENTS

| | | | | | |
|---|---|---|---|---|---|
| 3,290,894 | A | * | 12/1966 | Tsao | 62/216 |
| 4,099,923 | A | | 7/1978 | Milberger | |
| 4,221,568 | A | * | 9/1980 | Boettger | 436/48 |
| 4,816,121 | A | * | 3/1989 | Keefer | 204/156 |
| 5,039,489 | A | * | 8/1991 | Gleaves et al. | 422/68.1 |
| 5,959,297 | A | | 9/1999 | Weinberg et al. | |
| 6,004,617 | A | | 12/1999 | Schultz et al. | |
| 6,063,633 | A | * | 5/2000 | Willson, III | 436/37 |
| 6,149,882 | A | * | 11/2000 | Guan et al. | 422/211 |
| 6,306,658 | B1 | * | 10/2001 | Turner et al. | 436/37 |
| 6,485,692 | B1 | * | 11/2002 | Freitag et al. | 422/130 |

FOREIGN PATENT DOCUMENTS

| | | | |
|---|---|---|---|
| DE | 198 09 477 A1 | | 3/1998 |
| EP | 423294 | * | 4/1991 |
| GB | 2156381 | * | 10/1985 |
| GB | 2211201 | * | 6/1989 |
| WO | WO 99/21957 | | 5/1999 |
| WO | WO 99/64160 | | 12/1999 |

OTHER PUBLICATIONS

Cortes Corberan, V. et al, Industrial & Engineering Chemistry Product Research and Development 1984, 23, 546-552.*

Meusinger, J. et al, Journal of Catalysis 1995, 152, 189-197.*

Harrison, D. P. et al, Industrial and Engineering Chemistry 1965, 57, 18-24.*

Orkin, B. A., Industrial & Engineering Chemistry Product Research and Development 1969, 8, 154-160.*

Smigiel, W. A. et al, Industrial & Engineering Chemistry Fundamentals 1979, 18, 419-422.*

Snel, R., Industrial & Engineering Chemistry Fundamentals 1985, 24, 257-260.*

Lox, E. et al, Industrial & Engineering Chemistry Research 1988, 27, 576-580.*

Lucas, M. et al, Chemie-Ingenieur-Technik 1995, 67, 773-777.*

Stepanov, N. F., Zhurnal Fizicheskoi Khimii 1974, 48, 1531-1532.*

Belyi, A. S. et al, Neftekhimiya 1977, 17, 551-554.*

Greibrokk, T. et al, Analytical Chemistry 1984, 56, 2681-2684.*

Vit, Z. et al, Chemicky Prumysl 1988, 38, 449-452.*

Kunz, U. et al, Chemische Technik 1991, 43, 100-104.*

Zech, T. et al, Microreaction Technology: Industrial Prospects, Proceedings of the International Conference on Microreaction Technology, 3rd, Frankfurt, Apr. 18-21, 1999, 260-266, Editor: Ehrfeld, W., Publisher: Springer-Verlag, Berlin, Germany.*

Bublitz, D., Chemie-Anlagen+Verfahren 2001, 34, 86,88.*

Senkan, S.M., Nature, vol. 394 pp. 350-353.

Senkan, S.M. and Ozturk, S., Angewandte Chemie Int. Ed. 1999, 38, No. 6. pp. 791-794.

Cong, P. et al., Angewandte Chemie Int. Ed. 1999, 38, No. 4, pp. 483-488.

Jandeleit, B. and Weinberg, H., Chemistry & Industry, Oct. 1998, pp. 795-798.

* cited by examiner

PLURAL REACTION CHAMBER CATALYTIC TESTING DEVICE AND METHOD FOR ITS USE IN CATALYST TESTING

This is a request for filing a continuation application under 37 CFR 1.53(b) of pending prior international application No. PCT/ES01/00038, filed on Feb. 8, 2001 entitled A CATALYTIC TESTING DEVICE AND METHOD FOR ITS USE IN MATERIAL TESTING which designated the United States.

TECHNICAL FIELD OF THE INVENTION

This invention belongs to the technical field of analysis systems for chemicals and particularly to the sector of catalytic testing systems.

STATE OF THE ART PRIOR TO THE INVENTION

Advances in the chemical industry have largely been due to the development of new catalytic processes that make it possible to carry out production under especially adequate conditions of a range of chemicals such as medicines, polymers, fuels, etc. The key to the development of a catalytic process is, first of all, the availability of a catalyst that permits the reaction or set of reactions to take place under certain more interesting conditions from the point of view of economy, safety and versatility of the process. Nevertheless, the search for a specific catalyst is a costly task requiring the preparation of a large number of formulations, with their consequent testing in a reaction system. This entails very extensive periods of time until a suitable catalyst is successfully developed. The current trend is to reduce that time by means of using combinatory chemistry for accelerating the test and selection process. In general, this consists of the automated production of a combination of catalysts and a simultaneous testing of series of them.

The best way to carry out this type of catalytic testing is under realistic reaction conditions including temperature, pressure, streams, hydrodynamic and diffusion conditions, composition of feeds, etc., similar to those conditions that would be found in the industrial chemical process. To this, the tests that are currently conducted require certain systems that guarantee proper control of streams, temperatures and particularly pressure, which always leads to individual catalysis tests wherein the reactor houses only one catalyst. Thus, patent U.S. Pat. No. 4,099,923 describes a catalytic testing unit wherein, in spite of the fact that the test is individual, the reactor permits several catalysts to be housed, which are automatically tested one after another consecutively. The application for German patent DE-A-19809477 provides a reactor with different cavities where different catalysts are housed, permitting simultaneous testing but without achieving any kind of control or measure over the streams circulating through each catalyst, nor over the different temperatures. Moreover, the system described in that German patent application does not provide anything regarding the feed system for the products, pressure regulation, sample taking or subsequent analysis, all of them are fundamental aspects when it comes to having a suitable reaction system.

The patent application WO-A-99/64160 provides a system for the simultaneous testing of libraries of materials, permitting common feeding of a fluid to different vessels and a subsequent sequenced analysis of the outgoing fluids from each compartment. The fluid stream passing through each vessel is controlled by stream restrictors or stream controllers. For the distribution of flows, both at the inlet and at the outlet of the reactor, various switch valves are used. The main limitations of this system when it comes to achieving realistic reaction conditions are: (i) absence of automatic and dynamic pressure control, which would permit regulation of the pressure in all individual reactors and its possible variation during the course of the reaction tests; in addition to the fact that it is not possible to use them at high pressure; (ii) impossibility of varying the chemical composition of the feed currents for the different reaction compartments; (iii) absence of a prior conditioning stage for each individual feed current.

Moreover, the development of new techniques in combinatory chemistry (Senkan, S. M., Nature, vol. 394 pp. 350-353; Senkan, S. M. and Ozturk, S., Angewandte Chemie Int. Ed. 1999, 38, No 6, pp. 791-794; Cong, P. et al., Angewandte Chemie Int. Ed. 1999, 38, No 4, pp. 483-488; Jandeleit, B. and Weinberg, H., Chemistry & Industry, October 1998, pp. 795-798) have provided innovative units and methods (U.S. Pat. No. 5,959,297, U.S. Pat. No. 6,004,617 or WO 99/21957) for the quick and simultaneous testing of large libraries of catalysts. Nevertheless, in no way do these inventions guarantee acceptable conditions for catalytic testing according to the criteria stated above, yet on the contrary our reaction system does indeed guarantee this.

So, the subsequent chemical analysis required for the reaction products used by these new techniques of combinatory chemistry in general only permit an orientative idea to be gained of the catalytic activity.

The object of the present invention is a device capable of simultaneously conducting tests on materials or any type of physical or chemical process, with individual fluid feeds whose streams and compositions are fully controlled and measured at any moment of the process and which can be different for each reaction compartment. Also of importance is the prior conditioning stage for each individual feed current, the possibility of using gases, liquids and mixtures of them being of interest here.

Another object of the invention is a device of the type defined above with a pressure control permitting exact regulation of it in the array of reaction vessels and the possibility of its automatic variation during the experiment without the need to make changes in the device.

The invention also has as its object a multiple catalytic testing system that can work at a wide range of pressures in the reactor from sub-atmospheric values to pressure notably greater than the atmospheric one.

A further object of the invention is a multiple catalytic testing system allowing measurement both of the temperature that the material is at, during contact with the fed fluid, and of the pressure in each compartment, which permits a determination of the load loss of the circulating fluid occurring in that solid/fluid contact. Said data are of great importance for making sure that the conditions are those desired in the compartment, both in terms of safety conditions of the device and in terms of the need to know these data in order to make a correct evaluation of the properties of the materials, since the data quantify the physical and chemical contact between the material and the fluid.

It is therefore an objective of the present invention to provide an automated system and a method that permits catalytic activity tests on materials that might potentially be of interest for the catalysis of a particular chemical reaction or set of reactions. The system preferably permits the programmed development of the catalytic activity tests on a large number of materials simultaneously, thus achieving a saving of time, of investment on its construction, and of maintenance of the system, this being a major achievement to be pointed out in the invention.

A further objective of the invention is to provide a reactor and its accessories that make it possible the catalytic testing of multiple catalysts under conditions of temperature, pressure, streams and fluid feed composition permitting a reliable comparison to be made of catalytic activities among different materials, though also permitting different chemical and/or physical processes and/or chemical treatments to be performed on the said catalytic materials.

Another objective of the invention is to provide a method for conducting different catalytic tests, in such a way that the maximum amount of experimental data is obtained in the minimum length of time, at all times with a knowledge of the reaction conditions.

A further objective of the invention is to provide a system and a method of sample taking and quick quantitative analysis that make possible the continual sequenced analysis of the composition of the product gases coming from each compartment of the reactor, permitting operation at high pressures.

DESCRIPTION OF THE INVENTION

The objects and objectives specified above are achieved by means of an automatic device for catalytic testing which includes at least one reaction block (5) consisting of an array of reaction chambers (4) capable of housing solid materials inside and with each chamber having a fluid input, and an output connected to an outgoing fluid duct (24) that links up with analysis means (8) through the duct (22) (such as for example analysis means selected from among gas chromatography systems, mass spectrometry systems, visible spectrometry systems, ultraviolet spectrometry systems, infrared spectrometry systems and ultra-fast gas chromatography systems consisting of a set of capillary tubes arranged in columns selected from among columns of multiple capillaries in parallel and multicapillary columns, for the separation of different chemical compounds present in the outgoing fluid from each reaction chamber), fluid feed means (1, 10, 11) (such as for example a mass stream regulating system based on changes in temperature differences in the fluid, or a piston pump of the type used for HPLC systems), capable of performing regulated dosage of streams of at least one fluid with exactitude at a required pressure independently for each of the reaction chambers, the required pressure being common to each of the reaction chambers, automatic and dynamic pressure control means, capable of performing pressure regulation in each reaction chamber in conjunction with other reaction chambers, the control means consisting of at least a first non-return valve (23) provided in the outgoing fluid duct (24) between the outlet from each reaction chamber (4) and a common damping tank (6) that receives the outgoing fluid from each reaction chamber, a pressure sensor (3b) provided in a first outlet duct (25) and an automatic needle valve (20) provided in a second outlet duct (25) from the damping tank (6).

In accordance with the invention, the device can also comprise:

an automatic system for sample taking consisting of sample taking devices (13), in order to permit the regulated circulation of fluid from the outlet of any reaction chamber until the analysis means, a first temperature regulation system for regulating the temperature in each reaction block within a range from −20° C. to 800° C., preferably between 25° C. and 750° C., and which comprises at least one temperature sensor and at least one heating element, a conditioning system for the fluid fed to each reaction chamber, a second temperature regulation system for regulating the temperature in a range from 25° C. to 250° C., in at least part of the route of the fluids selected from among routes between the reaction block and the analysis means, between the system for fluid conditioning and the reaction block, in any part of the pressure control system, this second system comprising at least one temperature sensor and at least one heating element, a sample taking device for gathering samples from each reaction chamber, each system being arranged in a loop with a calibrated volume permitting the sample to be maintained at a defined temperature until a subsequent sequenced analysis is performed on the sample, the sample taking device displaying at least one loop, at least one switch valve, a temperature regulation system and at least one connection to the analysis means and to a sample taking device, a global control system for global control of the device, and/or a system for the management and handling of experimental data, selected from among temperatures, pressures, compositions, times and combinations of them.

The device of the invention is duly designed to withstand chemical and physical processes in a pressure range from 0.1 absolute atmospheres to 150 absolute atmospheres, preferably between 1.2 and 80 absolute atmospheres.

In an embodiment of the invention, the reaction chambers housed in the reaction block are removable and the reaction block is a massive block with openings for couplings to which the removable reaction chambers can be coupled.

The reaction block can in turn comprise a plurality of bodies thermally insulated from each other, with each body presenting an individual heating system and an individual temperature regulation system. This allows different sections or bodies at different temperatures to be had in the reaction block, if wished, thus making it possible to have a series of individual reactors at different temperatures.

Also, the reaction block can be designed in such a way that it is extractable, thereby making it possible for that block to be exchanged for another reaction block and/or other processes to be conducted on the materials housed inside this reaction block in another installation or in a different device.

The device of the present invention permits catalytic tests to be conducted with a wide range of reagents or mixtures (especially suited for catalytic experiments in oil refining, petrochemistry and chemistry, where the reactions can include mixtures of hydrocarbons coming from a real refinery stream), which can be in both the gaseous and liquid phase, under reaction conditions (temperature, pressure, contact time, hydrodynamic flow), comparable to those occurring in industrial processes. The possibility can be highlighted of working at pressures of up to 150 atmospheres thanks to the novel system of dynamic pressure regulation that has been developed. These aspects are considered to be highly relevant since they permit a quick and accurate decision to be taken on the suitability of a material for the catalysis of a chemical process at the industrial scale.

The amount of catalyst needed for carrying out a test can vary from 20 milligrams to 10 grams. In this way, it is not necessary to have large quantities of material available as usually occurs in conventional catalytic testing systems.

An innovative aspect is the achieving of automatic pressure control, thanks to a combination of different valves, tanks and other accessories, which will be described further below. The pressure range for which the installation and the control system itself have been designed lies between 0.1 absolute atmospheres up to 150 atmospheres, with the range preferably being from 1.2 atmospheres to 80 atmospheres. Moreover, the pressure can be varied automatically during an experiment, without any need to make changes in the device.

The reaction conditions can be maintained the same in all the reactions beds, since in each reactor tight control is exercised over the pressure, temperature and streams of the different flows making up the feed current for each reactor.

The present invention provides a device capable of simultaneously performing catalytic tests or tests or any other property of materials or any kind of physical or chemical process, with individual fluid feeds, whose streams and compositions are fully controlled at any moment of the process, and can be varied for each reaction compartment. Also important is the prior conditioning stage for each individual feed current, the possibility of using gases, liquids and mixtures of them for this purpose being of interest here.

The device permits the study both of the specific catalytic activity under certain fixed conditions and of more wide-ranging studies of chemical kinetics, including deactivation, studies in broad temperature ranges, regeneration; being included in the invention different categories of experiments with any sequence of temperatures in the reactor, pressures, streams of gases or liquids, or configuration of switch valves of the sample taking system.

On the other hand, the invention also refers to a method for the conducting of tests in devices of the type described above. Thus, the invention also refers to a method for using the device in catalytic tests of multiple catalysts wherein the magnitudes temperature, pressure of the reaction chambers along with streams and chemical composition of the feed current for all the reaction chambers are substantially equal and not varied over the time of the catalytic tests;

in catalytic tests of multiple catalysts wherein at least one magnitude selected from among temperature, pressure of the reaction chambers along with streams and chemical composition of the feed current for all the reaction chambers is temporarily varied in a programmed way;

in catalytic tests of multiple catalysts wherein the pressure in all the reaction chambers is substantially the same and wherein the temperature of the reaction chambers, the streams and chemical composition of the feed current for the reaction chambers can be different in each of the chambers;

in catalytic tests of multiple catalysts wherein from among N×M catalysts housed in the reaction block, only N catalysts are tested simultaneously, and this simultaneous test is repeated automatically M−1 times for the other catalysts, wherein N is at least 1; and a sequenced individual test being conducted when N is equal to 1;

in catalytic tests of multiple catalysts that undergo deactivation, during which consecutive individual tests of catalysts are performed in such a way that in a first stage only fluid is fed into a first reaction chamber and a sample of the outgoing fluid is taken constantly until the stabilisation of the deactivation curve of the catalyst becomes clear, in a second stage the feed of fluid in the first reaction chamber is stopped and a test similar to the first stage is conducted in a second reaction chamber, while the first reaction chamber is allowed to enter into the regeneration phase, an analogous sequence to that composed of the first and second stages is repeated successively with each ulterior reaction chamber chosen for the catalytic tests;

in catalytic tests wherein only one type of catalyst is housed in the reaction chambers;

for testing at least one property selected from among physical and chemical properties of a range of materials wherein the magnitudes of all the reaction chambers—temperature, pressure of the reaction chambers, as well as streams and chemical composition of the fluid current, which enters into contact with the material—are substantially equal in all the chambers and are not varied during the course of the test;

for testing at least one property selected from among physical and chemical properties of a range of materials wherein at least one of the magnitudes of all the reaction chambers—temperature, pressure of the reaction chambers, as well as streams and chemical composition of the fluid current, which enters into contact with the material—is temporarily varied in a programmed way;

in tests wherein the pressure is substantially equal in all the reaction chambers, wherein at least one condition chosen from among temperatures of the reaction chambers, streams and chemical composition of the fluid current, which enters into contact with the material, in at least one reaction chamber, is different from the conditions in the remaining reaction chambers;

in tests of N×M materials housed in the reaction block, wherein only N catalysts are tested simultaneously, and this simultaneous test is repeated automatically M−1 times for the remaining materials;

in tests where the reaction chambers house only one type of material;

for conducting processes selected from among physical processes, chemical processes and combinations of them, wherein the processes are selected from among synthesis of products, preparation of solid materials, regeneration of catalysts, and wherein the temperature, the pressure of the reaction chambers, as well as streams and the chemical composition of the fluid current, are substantially equal and are not varied during the course of the process;

for conducting processes selected from among physical processes, chemical processes and combinations of them, wherein the processes are selected from among synthesis of products, preparation of solid materials, regeneration of catalysts, and wherein the temperature, the pressure of the reaction chambers, as well as streams and the chemical composition of the fluid current, are temporarily varied in a programmed way jointly in all the reaction chambers;

for conducting processes selected from among physical processes, chemical processes and combinations of them, wherein the processes are selected from among synthesis of products, preparation of solid materials, regeneration of catalysts, and wherein the pressure in the all reaction chambers is substantially equal, and wherein the temperature, the streams and the chemical composition of the fluid current, of the reaction chambers are different one from another.

In accordance with what can be inferred from that stated above, the invention permits the development of multiple catalysis testing as simultaneous testing of all the different materials provided in the reaction block wherein the reaction conditions are identical in each of the individual reactors.

Similarly, the invention permits operation in the following manner: if one has N×M materials for testing, it is possible to conduct a simultaneous test of N materials and automatically repeat this test M−1 times for the N×(M−1) remaining materials, simply by properly programming: (i) the switching sequence of the sample taking valves and (ii) the control devices of the feed for each individual reactor.

The device of the invention can in turn be used for the rapid determination of the kinetics of a reaction, with deactivation processes being included here, with a single catalyst, simply by using the same catalyst in different chambers of the reactor and varying the reactions conditions in each one, with the exception of temperature and pressure. In the case wherein the reaction block consists of several bodies, it would then be possible to have a series of individual reactors at different temperatures since each body has its own temperature regulation system.

On the other hand, during the test on a series of catalysts it is possible to make a temporary programmed modification of the reaction conditions: flow through each individual reactor, composition of the feed, temperature of the feed, temperature of the material to be tested and pressure in the individual reactors.

For the case of studying reactions involving rapid deactivations of the catalyst, it is necessary to obtain a multitude of data on the composition of the fluid following contact with a certain catalyst, but during a short time period. With this end, it is possible to adapt the system of the invention for being able to conduct consecutive individual tests on catalysts, in other words, first only the fluid is fed into an individual reactor and a sample of the outgoing fluid is taken constantly until it becomes clear that the deactivation curve of the catalyst has stabilised, the feed of fluid in that individual reactor being then stopped, and the above test being conducted in a second reactor, while the first enters the phase of stripping, regeneration and stripping again. This same sequence is successively repeated with each of the reactors making up the reaction system. This process is performed automatically simply by means of properly programming the sequence of feed flows and switch valves. After that, regeneration can be carried out of the catalysts and their evolution can be followed only by continuing with the same system of sampling and analysis.

BRIEF DESCRIPTION OF THE FIGURES

Given below is a description of the invention complemented by means of some drawings wherein.

DESCRIPTION OF EMBODIMENTS OF THE INVENTION

Figure 1:
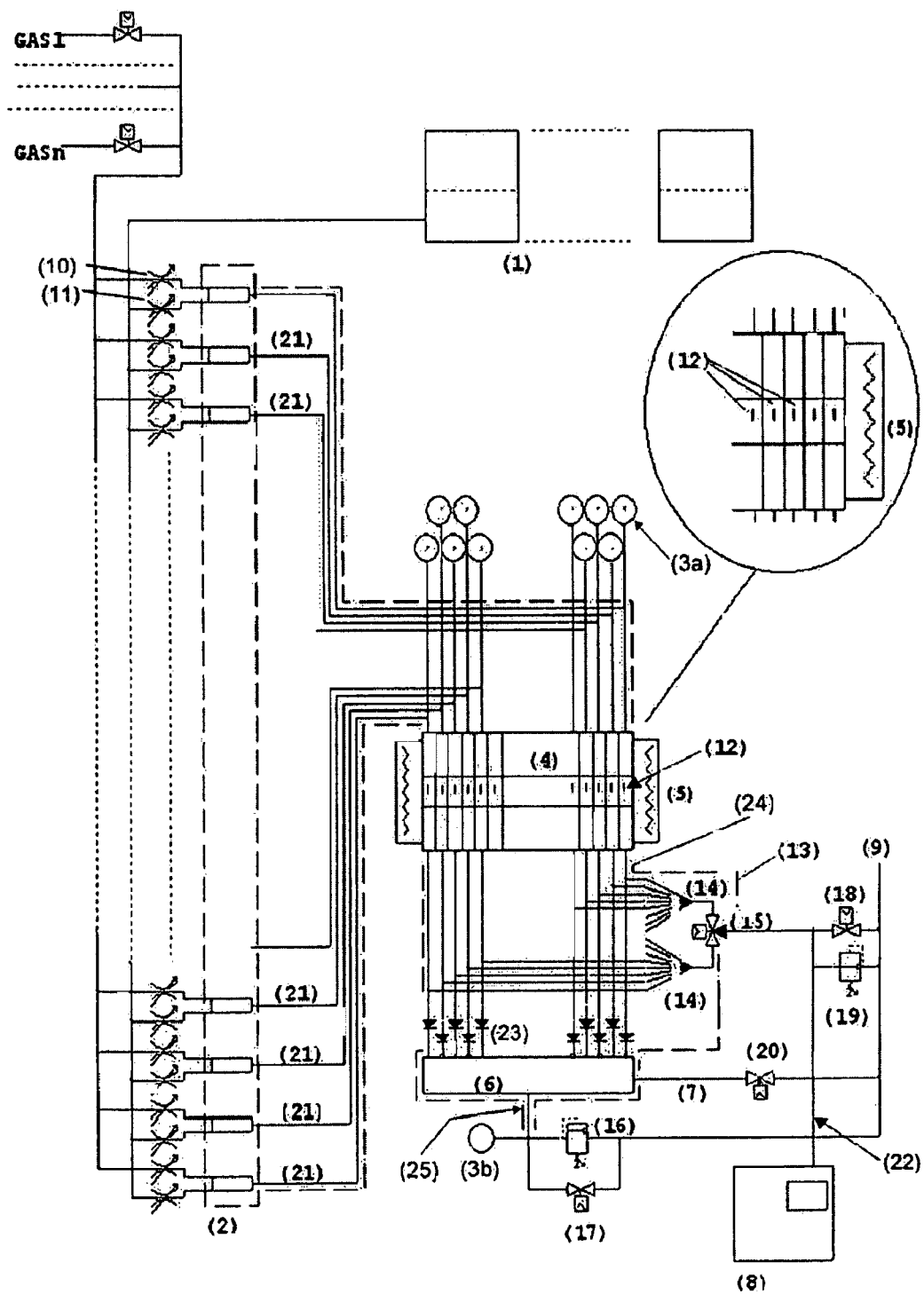
FIG. 1 is a hydraulic diagram of an embodiment of the device for simultaneous testing of multiple catalysts, in accordance with the present invention.

The figures include numerical references respectively denoting the following elements:
1 Vessels for gases and/or liquids
2 Heating device for the liquid and mixing of reagents with gases
3a and 3b Pressure sensors
4 reaction chambers
5 reaction block
6 damping tank
7 conduct to automatic needle valve
8 systems for chemical analysis of the products
9 discharge outlet for the system
10 stream measurement devices
11 stream regulation devices (10,11)
12 temperature measuring elements
13 sample taking devices
14 eight-way valve
15 three-way or three-position valve
16 safety valve (high pressure)
17 eight-way valve
18 eight-way valve
19 safety valve (low pressure)
20 needle valve for pressure regulation
21 ducts from the conditioning system to the reaction block
22 ducts from reaction block to the analysis system
23 non-return valves
24 outgoing fluid conduct from each reaction chamber
25 second outlet duct from the damping tank FIG. 1 shows a system incorporating an embodiment of the device according to the present invention which includes the following elements:

Vessels for gases and/or liquids (1).
Stream measurement and regulation devices (10,11), both for gases and for liquids; and pumping or evacuation means if necessary.
Heating device for the liquid and mixing of reagents with gases (2).
Reaction body or bodies (5), with the different chambers wherein the catalytic materials are housed.
Temperature measuring elements (12), and heating and thermal insulation elements; necessary for regulating the temperature in the preheater, in the reaction body and in those routes of the fluids wherein this is necessary in order to prevent cooling or condensation, as occurs in connections between the preheater and the different reaction chambers or the entire sample taking system as far as the analysis device or devices.
Pressure regulation device, including: non-return valves, a damping tank (6), automatic needle valves, pressure meters.
Sample taking devices (13): switch valve system (14,15).
Safety devices: safety valves (16,19).
Connection devices and accessories with the rest of the components.
System for chemical analysis of the products (8), such as might be gas chromatography, mass spectrometry, visible spectrometry, ultraviolet spectrometry and infrared spectrometry.
Control and regulation system for the global system.
Results management and handling system.

The reaction block (5) consists of one or several bodies made of a material permitting them to operate from sub-ambient temperature (−20° C.) up to temperatures of 800° C., with preference being given to a material with a high thermal conductivity, preferably bronze or stainless steel, wherein multiple reaction chambers of individual reactors (4), preferably of a cylindrical shape are housed, wherein the different materials for their catalytic testing or other kind of physical and/or chemical treatment are placed.

The reaction block (5) permits charging and discharging of the series of materials. The block (5) can also be constructed in such a way that it can be removed and extracted in a simple manner, either for being replaced by another reaction block or for carrying out other processes on the solid materials housed inside the reaction block in another installation or different device.

Each reaction chamber or individual reactor (4) has a feed current consisting of a gas and/or liquid or a mixture of liquids, which are conditioned to the necessary temperature, pressure and state of aggregation (gas, liquid or supercritical fluid) before being introduced in that reaction chamber. So, the system has as many feed currents as chambers, and the dosage and conditioning are therefore fully independent for each of them. The gas or gases are dosed by a mass stream automatic system (10, 11). In the case of using liquids, these are driven by a pump, or they are pressurised and their stream is regulated by systems analogous to those used with gases. After that, the liquids are conditioned, in other words, they are preheated and, if necessary, vaporised and mixed with the gases. To this effect, the device has a heating device (2) with multiple compartments and which possesses a heating system with thermocouples for thermal regulation.

Each individual current is then forced to pass through a reaction chamber or individual reactor (4) housed in the reaction block (5), which is at a defined pressure and temperature, wherein the catalytic reaction (test) or other modification process for the material being investigated is going to take place. The material can be provided in the form of a bed of solid granules of different sizes or in the form of porous solid blocks.

The fluids coming from the reaction of all the reaction chambers flow then to a common damping tank (6) for all the outgoing currents, which is connected to an automatic needle valve (7) which evacuates the common fluid constantly in a stream that permits tight control over the pressure of the fluid in the array of reaction chambers. The purpose of this tank is to make sure that the pressure at the outlet from all the reaction chambers is exactly the same, and to damp any perturbation in the flows thereof. With this shared pressure control, the system can be made more cheaply than by using various reactors separately. The pressure range for which the installation and the control system itself have been designed lies between 0.1 absolute atmospheres up to 150 atmospheres, with the range preferably being from 1.2 atmospheres to 80 atmospheres. Moreover, the pressure can be automatically varied during an experiment, without any need to make changes in the device.

By means of a system of automatic switch valves (13,14, 15), samples are alternately taken from the outgoing currents of each of the different individual reactors, which flow to the chemical analyser or analysers of the fluid that was in contact with a material in the reaction chamber, in such a way that the time necessary for taking the sample and switching between valves is minimised. Before passing to the analysis system, the fluid passes through an automatic needle valve (20) in such a way that: (i) the pressure of the fluid is reduced, since the detection systems generally require pressures close to atmosphere; (ii) a stream of the outgoing current from the chosen individual reactor is selected in such a way that the conditions of the flow via this reactor are scarcely affected by the sample taking at a point. In the same way, the pressure is properly maintained in the reactor without involving the distribution system for flows used in the analysis system.

It is also possible to carry out simultaneous sampling of several individual reactors by means of adapting the switch valves, connections and automatic needle valves.

The analysis can be performed, for example, by means of one or several of the techniques: gas chromatography, mass spectrometry, visible spectrometry, ultraviolet spectrometry or infrared spectrometry.

All the elements of the automatic device can be controlled by an electronic PLC (programmable logic controller) device which in turn communicates with a PC compatible computer.

The PLC contains the PID temperature control algorithms for the different heaters and is in charge of sending the computer the different physical magnitudes present in the equipment as well as handling the different actuators thereof.

For pressure control it is also necessary to have a control loop of the PLC which uses a pneumatic needle valve as an actuator and a pressure sensor for measuring the outlet variable from the physical system, this being the magnitude to be controlled.

The sequence of stages that have to be carried out in the catalytic testing experiment are programmed from the computer along with the selection of the preset values for the difference physical magnitudes of the system: liquid streams, gas streams, temperatures of the preheats, temperature of the reaction body, pressure, etc.

Also determined from the computer are the safety margins for each magnitude. In this way, if any of these are exceeded, different safety actions or procedures are triggered which, depending on the case, can range from an mere indication of an alarm situation up to shutdown of the process even.

Figure 2:
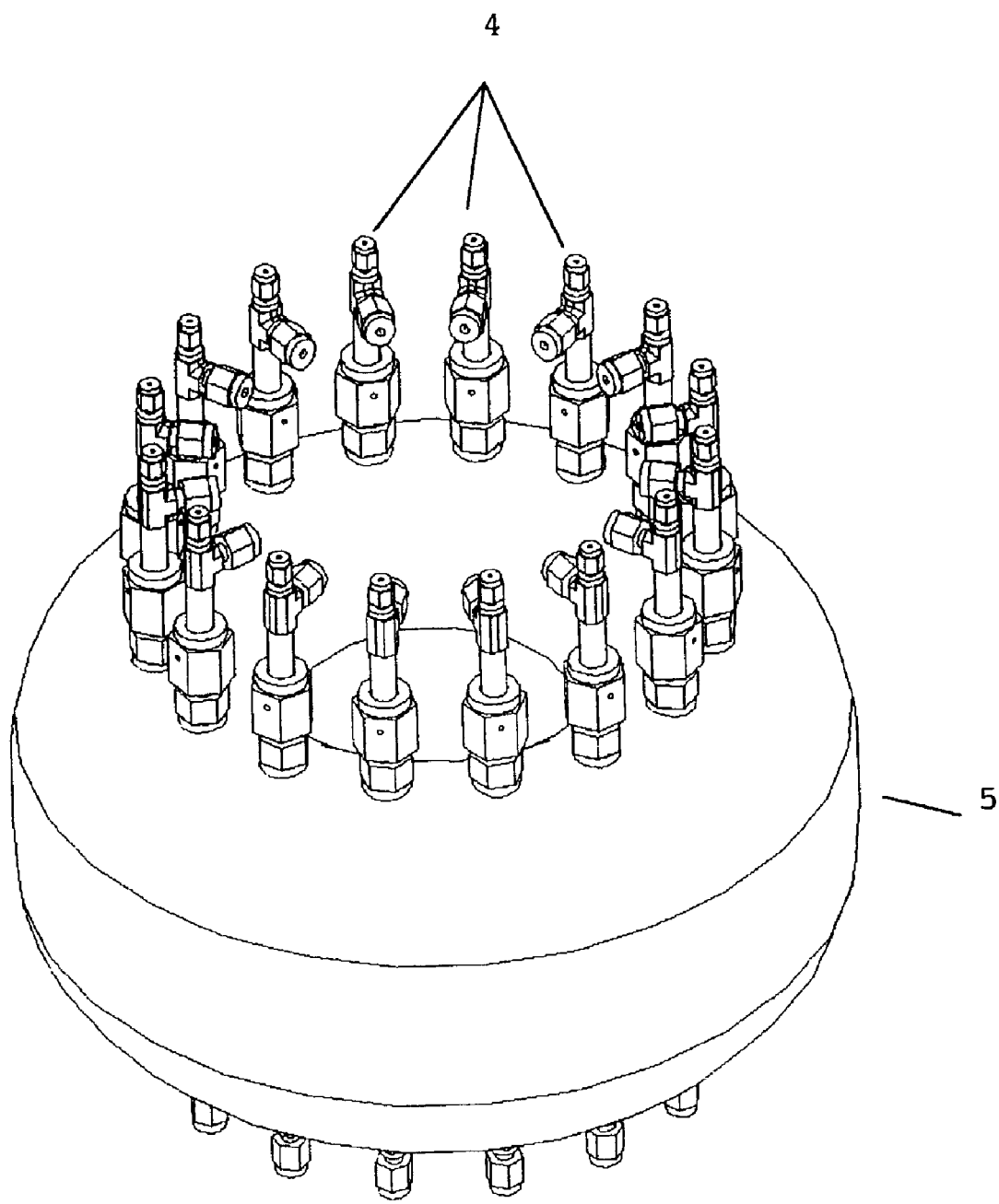
FIG. 2 is a schematic view of the reaction block of a device for simultaneous testing of sixteen catalysts, in accordance with an embodiment of the present invention.

An example of an automatic device in accordance with the invention could be the conducting of a test on sixteen types of solid zeolite catalysts placed in separate compartments (4), housed in a reaction block (5) (see FIG. 2), all of which are at the same pressure and temperature. The reaction block is composed of a single body provided with a heating and thermal regulation system.

The feed for each individual reactor consists of a liquid and a gas, to be chosen from among nitrogen, air and hydrogen, which is dosed by an automatic controller. The liquid, which is pressured in a tank, is also dosed by a stream controller. The liquid is vaporised in the heating device at the same time as being mixed with the gas. The temperature required for ensuring the phase change will depend both on the total pressure of the individual reactors and on the final vapour/gas ratio.

The reaction can be carried out, for example, up to a temperature of seven hundred degrees centigrade. The outlet from the reaction system as far as the analysis equipment has to be heated in order to prevent condensation of vapours in the ducts or the valve bodies. In the same way, the connection section between the heating device and the individual reactors is duly heated for the same reason.

The volume of catalyst that is possible to use in each reaction bed is up to ten cubic centimetres.

FIG. 1 shows a hydraulic diagram. In it can be seen that the eight outlets from the reactor are connected to a damping tank by means of a non-return valve which prevents the backflow of gases from the tank to the reaction block or to the sample taking system. The sample taking for the chemical analysis is done by means of three valves: two with eight inlets and one outlet, and one with two inlets and one outlet.

A measurement is made of the pressure and temperature in each reaction bed. The measurement of both the temperature that the catalyst is at during contact with the feed fluid and the load loss of the circulating fluid that occurs in that solid/fluid contact is of great importance for ensuring that the reaction conditions are those desired for reasons of both reliability of the results and safety of the device. But, moreover, this data can even be of interest for evaluating the properties of the materials since they quantify the physical and chemical contact between the material and the circulating fluid.

With this arrangement of valves, it may be achieved that the outlet from one of the individual reactors via one of the first two valves is being analysed, while the other valve is being positioned, and the following outlet from the reactor can be analysed with a rapid change of the two-position valve.

In the outlet from the damper tank, as well as in the connection of the analyser, there are some safety valves provided which open in the event of the pressure exceeding the pre-established limits.

The different elements of the reactor are entirely manufactured from quartz, glass and/or stainless steel, in order to prevent atmospheric corrosion at high temperatures.

The temperature of the reaction block and the preheaters or heating devices is achieved by means of using a system of individual or common heating for the sixteen feeds and catalytic beds.

All the elements of this automatic device are controlled by an electronic PLC (programmable logic controller) device which in turn communicates with a PC compatible computer.

The PLC contains the PID temperature control algorithms for the different heaters and is in charge of sending the computer the different physical magnitudes present in the equipment as well as handling the different actuators for it.

The sequence of stages that have to be carried out in the catalytic testing experiment are programmed from the computer along with the selection of the preset values for the difference physical magnitudes of the system: liquid streams, gas streams, temperatures of the preheaters, temperature of the reaction body, pressure, etc. The computer program also permits the handling and management of experimental data with the use of formats in files and data that are compatible with standard software.

The invention claimed is:

1. An automatic catalytic testing device comprising
   at least one reaction block (5) which comprises a set of reaction chambers (4) capable of housing solid materials in their interior and each chamber (4) comprising a fluid inlet, and an outlet connected to an outgoing fluid duct (24) which communicates with analysis means (8) through duct (22),
   means of fluid feed (1, 10, 11) capable of performing regulated dosing of flows of at least one fluid with exactitude at a required pressure independently in each of the reaction chambers (4), said required pressure being common to each of the reaction chambers,
   automatic and dynamic pressure control means, capable of performing pressure regulation in each reaction chamber in conjunction with other reaction chambers, the pressure control means comprising at least a first non-return valve (23) provided in the outgoing fluid duct (24) between the outlet for each reaction chamber and a common damping tank (6) that receives the outgoing fluid from each reaction chamber (4), a pressure sensor (3b) provided in a first outlet duct (25) and an automatic needle valve (20) provided in a second outlet duct, and
   sample taking devices (13) for sample taking, in order to permit the regulated circulation of fluid from the outlet of any reaction chamber as far as the analysis means.

2. A device according to claim 1, comprising at least one temperature sensor (12) in at least one reaction chamber.

3. A device according to claim 1, comprising at least one pressure sensor (3a) in at least one reaction chamber (4).

4. A device according to claim 1, wherein the fluid feed means consist of a mass stream regulating system based on changes in temperature differences in the fluid.

5. A device according to claim 1, wherein the fluid feed means consist of a piston pump of the type used for HPLC systems.

6. A device according to claim 1, further comprising a first temperature regulation system for regulating the temperature in each reaction block within a range from −20° C. to 800° C., and which comprises at least one temperature sensor and at least one heating element.

7. A device according to claim 6, wherein the first temperature regulation system permits regulation of the temperature between 25° C. and 750° C.

8. A device according to claim 1, comprising also a conditioning system of the fluid fed to each reaction chamber (4).

9. A device according to claim 1, further comprising a second temperature regulation system for regulating the temperature in a range from 25° C. to 250° C., in at least part of the route of the fluids selected from among routes:
   between the reaction block (5) and the analysis means (8),
   between the system for fluid conditioning and the reaction block (5),
   in any part of the pressure control system,
   this second system including at least one temperature sensor and at least one heating element.

10. A device according to claim 1, designed to withstand chemical and physical processes in a pressure range from 0.1 absolute atmospheres to 150 absolute atmospheres.

11. A device according to claim 1, wherein the analysis means (8) is selected from among gas chromatography systems, mass spectrometry systems, visible spectrometry systems, ultraviolet spectrometry systems, infrared spectrometry systems and ultra-fast gas chromatography systems.

12. A device according to claim 11, wherein the ultra-fast gas chromatography system consists of a plurality of capillary tubes arranged in columns selected from among columns of multiple capillaries in parallel and multicapillary columns, for the separation of different chemical compounds present in the outgoing fluid from each reaction chamber.

13. A device according to claim 1, further comprising taking devices (13) for gathering samples from each reaction chamber (4), each device being arranged in a loop with a calibrated volume permitting the sample to be maintained at a defined temperature until a subsequent sequenced analysis is performed on the sample, the sample taking devices (13) displaying at least one loop, at least one switch valve, a temperature regulation system and at least one connection to the analysis means and to the sample taking devices (13).

14. A device according to claim 1, wherein the reaction chambers (4) housed in the reaction block (5) are removable, and the reaction block (5) is a massive block with coupling openings wherein the removable reaction chambers (4) are coupled.

15. A device according to claim 1, wherein the reaction block (5) includes a range of bodies thermally insulated from each other, with each body presenting an individual heating system and an individual temperature regulation system.

16. A device according to claim 1, wherein the reaction block (5) is extractable.

17. A device according to claim 1, further comprising includes a global control system for the device.

18. A device according to claim 1, further comprising a system for the management and handling of experimental data, selected from among temperatures, pressures, compositions, times and combinations of them.

19. A method for using a device according to claim 1, in catalytic tests of multiple catalysts comprising feeding materials to the reaction chambers, carrying out a physical or chemical process in said reaction chambers and analyzing the products of said process, and wherein the magnitudes of the temperature and pressure of the reaction chambers along with streams and chemical composition of the feed current for all the reaction chambers (4) are substantially equal and not varied over the length of time of the catalytic tests.

20. A method for using a device according to claim 1, in catalytic tests of multiple catalysts comprising feeding materials to a set of reaction chambers, carrying out a physical or chemical process in said reaction chambers and analyzing the products of said process, and wherein at least one magnitude selected from among temperature, pressure of the reaction chambers along with streams and chemical composition of the feed current for all the reaction chambers (4) is temporarily varied in a programmed way.

21. A method for using a device according to claim 1, in catalytic tests of multiple catalysts comprising feeding materials to a set of reaction chambers, carrying out a physical or chemical process in said reaction chambers and analyzing the products of said process, and wherein the pressure in all the reaction chambers (4) is substantially the same and wherein the temperature of the reaction chambers (4), the streams and chemical composition of the feed current for the reaction chambers (4) can be different in each of the chambers.

22. A method for using a device according claim 1, in catalytic tests of multiple catalysts comprising feeding materials to a set of reaction chambers, carrying out a physical or chemical process in said reaction chambers and analyzing the products of said process, and wherein from among N×M catalysts housed in the reaction block (5), only N catalysts are simultaneously tested, and this simultaneous test is automatically repeated M−1 times for the remaining catalysts, wherein N is at least 1; and a sequenced individual test being conducted when N is equal to 1.

23. A method for using a device as defined in claim 1 comprising feeding materials to a set of reaction chambers, carrying out a physical or chemical process in said reaction chambers and analyzing the products of said process, capable of simultaneously conducting tests on the products of said physical or chemical process, with individual fluid feeds whose streams and compositions are fully controlled and measured at any moment of the process.

24. A method according to claim 23, in catalytic tests of multiple catalysts that undergo deactivation, during which consecutive individual tests of catalysts are performed in such a way that
  in a first stage only fluid is fed into a first reaction chamber (4) and a sample of the outgoing fluid is taken constantly until the stabilisation of the deactivation curve of the catalyst becomes clear,
  in a second stage the feed of fluid in the first reaction chamber (4) is stopped and a test similar to the first stage is conducted in a second reaction chamber (4), while the first reaction chamber (4) is allowed to enter into the regeneration phase,
  an analogous sequence to that composed of the first and second stages is successively repeated with each ulterior reaction chamber (4) chosen for the catalytic tests.

25. A method according to claim 23, in catalytic tests wherein only one type of catalyst is housed in the reaction chambers (4).

26. A method for using a device according to claim 23, wherein at least one property selected from among physical and chemical properties of a range of material is tested, and the magnitudes of all the reaction chambers (4), selected from among temperature, pressure of the reaction chambers, as well as streams and chemical composition of the fluid current, which enters into contact with the material, are substantially equal in all the chambers and are not varied during the course of the test.

27. A method according to claim 26, in tests of N×M materials housed in the reaction block, wherein only N catalysts are simultaneously tested, and this simultaneous test is automatically repeated M−1 times for the other materials.

28. A method according to claim 26, in tests wherein the reaction chambers house only one type of material.

29. A method for using a device according to claim 23, wherein at least one property selected from among physical and chemical properties of a range of materials is tested, and wherein at least one of the magnitudes of all the reaction chambers (4), selected from among temperature, pressure of the reaction chambers, as well as streams and chemical composition of the fluid current, which enters into contact with the material, is temporarily varied in a programmed way.

30. A method according to claim 23, in tests wherein the pressure is substantially equal in all the reaction chambers, wherein at least one condition chosen from among temperatures of the reaction chambers (4), streams and chemical composition of the fluid current, which enters into contact with the material, in at least one reaction chamber (4), is different from the conditions in the other reaction chambers (4).

31. A method for using a device according to claim 23 for conducting processes selected from among physical processes, chemical processes and combinations of them wherein the processes are selected from among synthesis of products, preparation of solid materials, regeneration of catalysts, and wherein the temperature, the pressure of the reaction chambers, as well as streams and the chemical composition of the fluid current, are substantially equal and are not varied during the course of the process.

32. A method for using a device according to claim 1 for conducting processes selected for among physical processes, chemical processes and combinations of them, comprising feeding materials to a set of reaction chambers, carrying out a physical or chemical process in said reaction chambers and analyzing the products of said process, wherein the processes are selected from among synthesis of products, preparation of solid materials, regeneration of catalysts and wherein the temperature, the pressure of the reaction chambers (4), as well as streams and the chemical composition of the fluid current, are temporarily varied in a programmed way jointly in all the reaction chambers (4).

33. A method for using a device according to claim 1, for conducting processes selected from among physical properties, chemical processes and combinations of them, comprising feeding materials to a set of reaction chambers, carrying out a physical or chemical process in said reaction chambers and analyzing the products of said process, wherein the processes are selected from among synthesis of products, preparation of solid materials, regeneration of catalysts, and wherein the pressure in the reaction chambers (4) is substantially equal, and wherein the temperature, the streams and the chemical composition of the fluid current, of the reaction chambers (4) are different one from another.

* * * * *